United States Patent [19]

White

[11] Patent Number: 4,612,012
[45] Date of Patent: Sep. 16, 1986

[54] CORNEAL IMPLANT

[76] Inventor: Thomas C. White, 1127 Holly Dr., Sioux Falls, S. Dak. 55705

[21] Appl. No.: 402,740

[22] Filed: Jul. 28, 1982

[51] Int. Cl.⁴ ............................................. A61F 2/14
[52] U.S. Cl. ........................................................ 623/5
[58] Field of Search ............................ 3/13; 623/4–6

[56] References Cited

U.S. PATENT DOCUMENTS

| 2,517,523 | 8/1950 | Batchelder | 3/13 |
| 2,754,520 | 7/1956 | Crawford | 3/13 |
| 3,074,407 | 1/1963 | Moon et al. | 3/13 X |
| 3,458,870 | 8/1969 | Stone | 3/13 |
| 3,866,249 | 2/1975 | Flom | 3/13 |
| 3,945,054 | 3/1976 | Federov et al. | 3/13 |
| 4,025,965 | 5/1977 | Siegmund | 3/13 |

FOREIGN PATENT DOCUMENTS

| 2705234 | 8/1978 | Fed. Rep. of Germany | 3/13 |
| 1577825 | 10/1980 | United Kingdom | 3/13 A |

OTHER PUBLICATIONS

"Implantation Of An Artificial Cornea" by M. A. Torres et al., American Journal of Ophthalmology, vol. 56, No. 6, Dec. 1963, pp. 937–941.

Primary Examiner—Ronald L. Frinks
Attorney, Agent, or Firm—James R. Haller; Gregory P. Kaihoi

[57] ABSTRACT

Surgical replacement of all or a portion of the cornea may be performed through the use of an implant having a central lenticular portion, and a peripheral portion having an outer tissue contacting surface of a biologically compatible material. The peripheral portion protects eye tissue from contact with the lenticular portion.

9 Claims, 20 Drawing Figures

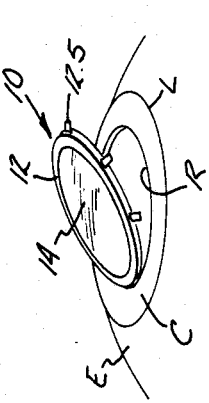
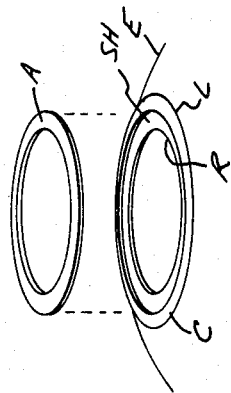
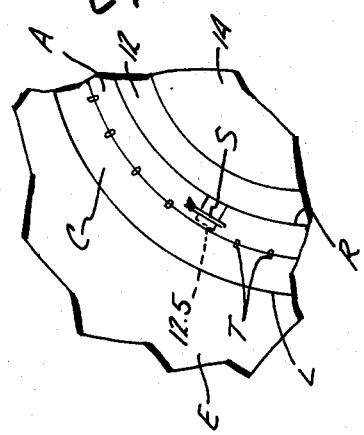
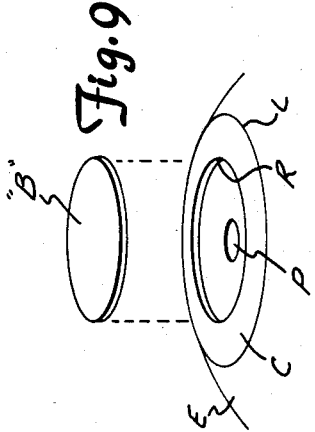
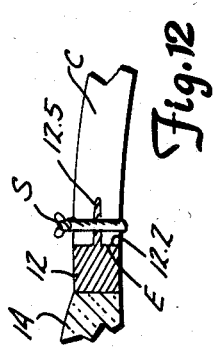
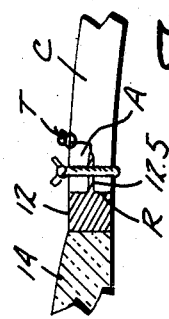
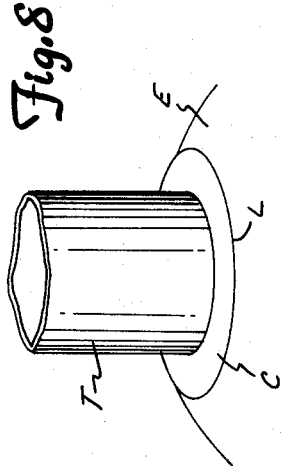
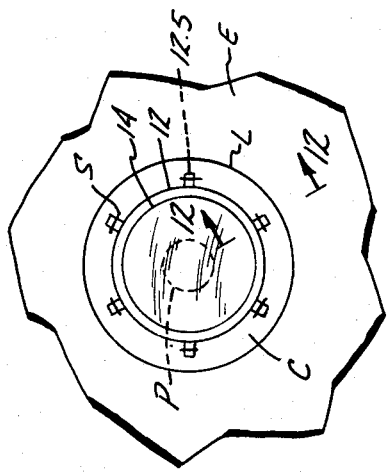

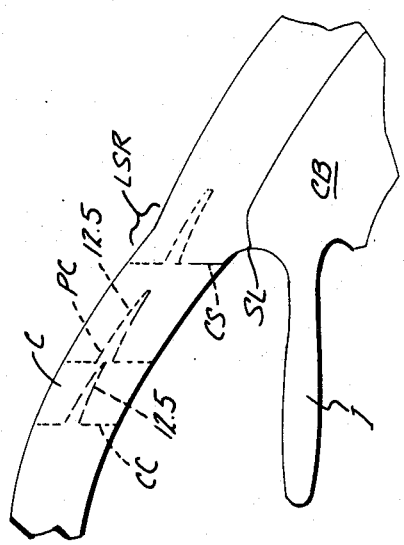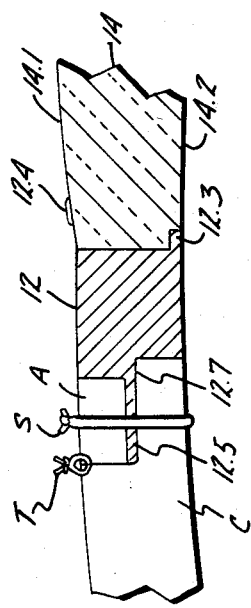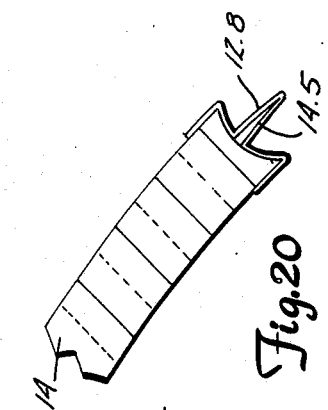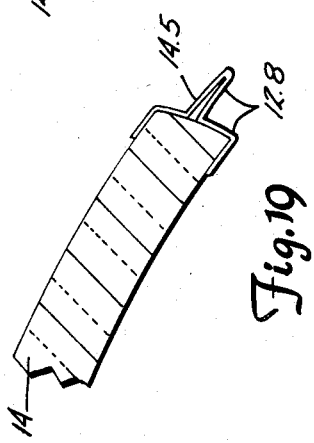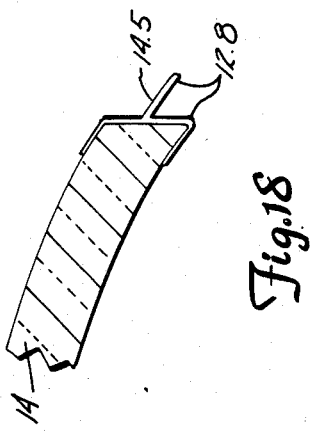

CORNEAL IMPLANT

FIELD OF THE INVENTION

The invention relates to prosthetic devices, and particularly to such devices as may be employed to replace damaged corneal tissue.

BACKGROUND OF THE INVENTION

For various reasons, the corneal portions of eyes must be surgically replaced. For example, the cornea may become scratched or scarred or otherwise physically damaged, greatly hindering sight. The cornea is also subject to affect by various degenerative diseases, mandating replacement if the patient is to have normal or even near normal vision. Corneal transplants have become quite common in the United States, particularly with the advent of microsurgery. Unfortunately, donor corneas are very difficult to obtain. A cornea to be donated must be employed, if at all, within a matter of days or weeks from the time of death of the donor. Although eye banks have been organized throughout the United States, one cannot rely upon the availability of a donor at the time it is needed for a transplant operation. As a result, vision, which could have been wholly or partially restored in many patients, is often permanently lost.

DESCRIPTION OF THE PRIOR ART

Attempts have been made in the past to utilize artificial materials for corneal transplants. Representative of such attempts are those reported in Barraquer, *Queratomileusis y Queratofaquia,* Instituto Barraquer de America, Bogata, Col. 1980, and Yasuji, *Research on Transplantation of Cornea Artificialis,* Proc. Japan Opthal. Soc. 1950 (Abstract). For the most part, the implantation of artificial corneal materials has at best been a temporary, stop-gap measure taken to seal the anterior chamber of the eye for a period of time until a donor cornea could be located for transplantation. As with other parts of the human body, the eye tends to reject and eject or extrude foreign materials during the healing process, with the result that the implantation of artificial corneas generally leads to loss by ejection of the cornea, to further eye damage and to leakage of aqueous humor from the anterior chamber.

SUMMARY OF THE INVENTION

In one embodiment, the invention relates to an implantable corneal prosthesis which comprises a lenticular transparent central portion of a biologically acceptable material, and a peripheral portion having an outer, tissue-contacting surface of a material that is biologically compatable with the eye tissue contacted by it after implantation. The peripheral portion is configured to protect the lenticular portion from contact with eye tissue. Attachment means are preferably provided for attaching the ring to the rim of tissue remaining after surgical removal of all or a portion of the cornea from the eye. In the preferred embodiment, the tissue-contacting surface of the peripheral portion is of a material, such as gold, platinum, polymers or other material that is not only biologically compatable but which in addition supports the adherence of the adjacent eye tissue thereto.

In another embodiment, the invention relates to a method of surgical placement of an artificial cornea in an eye which comprises the steps of removing all or a portion of the natural cornea from the eye, leaving a generally circular rim, providing an implantable corneal prosthesis having a lenticular, central portion, and a peripheral portion having an outer, tissue-contacting surface of a material that is biologically compatable with the rim of eye tissue, the periphery being configured to protect the disc from contact with the corneal tissue of an eye and including attachment means for attaching the ring to the rim of eye tissue, and placing the prosthesis centrally within the rim of tissue and attaching the attachment means to and within the rim of tissue.

In a preferred embodiment, the attachment means comprises a flange or flanges extending outwardly of the prosthesis generally parallel to the surface of the eye wall adjacent the tissue rim. The method desirably includes the step of inserting the flange means laterally within the thickness of the rim so that the flange or flanges are substantially completely imbedded in the thickness of the rim, preferably within the anterior two-thirds of such thickness. This may be accomplished by stretching the rim slightly during the surgical placement of the prosthesis. This may also be accomplished by removing a partial thickness annular section of cornea or scleral tissue from the rim, placing the prosthesis device within the opening with its outwardly extending flange or flanges resting upon the remaining thickness of the rim, and then replacing the removed annular section upon the flange or flanges. Suturing is provided, as necessary. It will be understood that the entire tissue-contacting surface of the prosthesis, including the attachment means, is of a biologically acceptable material which is not subject to rejection or ejection by eye tissue and which will support the adherence of eye tissue thereto as the healing process proceeds.

In each of the embodiments of the invention, the peripheral portion of the prosthesis serves as a barrier between tissue of the adjacent tissue rim and the generally transparent lenticular portion; that is, by employing a peripheral portion having a tissue-contacting surface that is not ejected or rejected by the eye, the lenticular portion of the prosthesis is maintained out of contact with the tissue corneal rim and no ejection or rejection of the prosthesis as a whole occurs. During the healing process, ingrowth of the rim tissue onto the peripheral outer surface more securely holds the prosthesis in place.

BRIEF DESCRIPTION OF THE DRAWINGS

FIG. 8 is a perspective, diagramatic view showing a step in a method of the invention;

FIGS. 9 and 10 are views similar to that of FIG. 8 showing further steps in a method of the invention;

FIG. 11 is a top view of a prosthesis of the invention, shown broken-away and mounted to an eye of a patient;

FIG. 12 is a cross-sectional broken-away view taken along line 12—12 of FIG. 11;

FIG. 13 is a perspective, diagramatic view showing a step in a modified method of the invention;

FIG. 14 is a broken-away, cross-sectional view showing another step in a modified form of the method;

FIG. 15 is a top view, broken-away and similar to that of FIG. 11, showing a step in a modified method of the invention.

FIG. 16 is a view similar to that of FIG. 14 but showing a modified embodiment;

FIG. 17 is a broken-away, schematic anatomical view of the eye; the locations of prosthesis of the invention shown in dashed lines;

FIG. 18 is a broken-away, cross-sectional view of a modified prosthesis;

FIG. 19 is a view similar to FIG. 18 but showing another modification; and

FIG. 20 is a view similar to FIG. 18 but showing yet another modification.

DESCRIPTION OF THE PREFERRED EMBODIMENT

Figure 1:
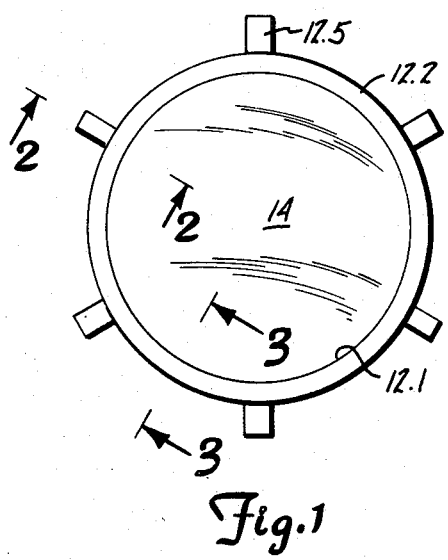
FIG. 1 is a plan view of a prosthesis of the invention.
Figure 2:
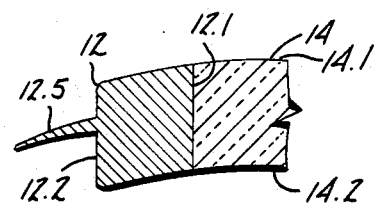
FIG. 2 is a partially broken-away, cross-sectional view taken along line 2—2 of FIG. 1.
Figure 3:
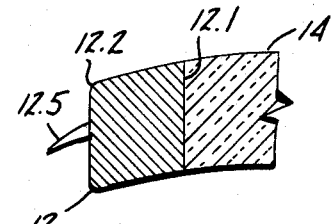
FIG. 3 is a partially broken-away, cross-sectional view taken along line 3—3 of FIG. 1.

With reference to FIGS. 1-3, a device of the invention is shown generally as (10) and includes a central transparent lenticular portion (14) and a peripheral portion typified by a ring or circular frame (12). The prosthesis may be mounted in the eye as a corneal replacement as shown in FIGS. 8-12, the peripheral portion (12) spacing the lenticular portion (14) from the eye tissue and having a biologically compatible outer surface (12.2) that solely is in contact with eye tissue.

By "biologically compatible," reference is made to materials that are not ejected from eye tissue nor provoke immune responses, all as described more fully below. One such material is substantially pure gold. Platinum and certain silicones may also be biologically compatible. Desirably, the outer, tissue-contacting surface also supports the growth of eye tissue thereon; exemplary of such materials is substantially pure gold and alloys of high gold content, and the surface preferably is burnished. The choice of a biologically acceptable material may depend upon the portion of the eye wall to which it is to be attached, in that the corneo-scleral portion of the eye appears to be more tolerant of foreign material than the peripheral corneal area which in turn is more tolerant than the central corneal area.

The biological compatibility of the peripheral surface of the prosthesis is of great importance in the substantially permanent acceptance of the prosthesis by the eye, and provides a strong, liquid-tight seal between the prosthesis and the eye wall to seal the anterior chamber.

Figure 4:
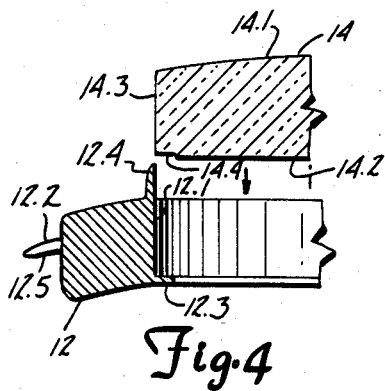
FIG. 4 is a diagramatic view, in partial cross-section and partially broken-away, showing assembly of a prosthesis of the invention.

As shown in FIGS. 2-4, the ring (12) may have a generally rectangular, or, preferably, a parallelogram configuration in cross-section, the inner periphery of the ring being generally perpendicular to its plane so as to provide surface-to-surface contact with the outer periphery of the disc-like lenticular portion (14). Similarly, the outer periphery (12.2) of the ring preferably also is generally perpendicular to the plane of the ring so as to provide generally surface-to-surface contact between it and the generally flat edge "E" (FIG. 12) of the rim of tissue remaining after surgical removal of all or a portion of the cornea. Other cross-sectional configurations, of course, can also be employed.

As shown in FIG. 4, the ring may have an inwardly protruding rim (12.3) forming an annular shoulder at one edge of the ring upon which the periphery of the disc (14) may seat when the ring (12) and disc (14) are assembled.

The thickness of the ring is desirably chosen to be approximately the same as the thickness of the corneal tissue to which it is to be attached. The thickness of the ring (measured radially of the prosthesis) is sufficient to provide the ring with resistance to deformation from the forces encountered during implantation.

The disc-like lenticular portion (14) may be made of any substance that is biologically acceptable (that is, that does not introduce harmful foreign substances into the eye), and the preferred material is polymethyl methacrylate. The disc desirably has a slightly domed outer surface (14.1) to simulate the natural curvature of the surgically removed corneal portion. Its interior surface (14.2) may be configured as desired, and may be generally planar as shown in the drawings or slightly concave if desired. Also, the disc may be so configured as to act as a lens and to provide a visual correction for the eye. The outer periphery (14.3) of the disc desirably is generally flat so as to provide surface-to-surface contact between it and the ring. If desired, the edge of the disc may be recessed slightly as shown at (14.4) in FIG. 4 to receive the rim (12.3) of the ring.

The disc (14) desirably is adhesively attached within the ring (12), and various biologically acceptable adhesives such as dental adhesives are known. The adhesive may be employed between the mating surfaces of the ring and disc, the adhesive being chosen not only for its bonding properties, but also for its biological acceptability. The adhesive should be resistant to aqueous humor and to tear fluid, and should not contain materials that might be leached from the prosthesis. The disc may be mechanically attached to the ring by means of the rim (12.3), as described above, and also by means of bendable fingers or prongs (12.4) shown best in FIG. 4, the fingers arising from the inner periphery of the ring and being bent over into contact with the upper surface (14.1) of the disc when the disc and ring are assembled. Desirably, a plurality of fingers (12.4) are employed and are spaced equiangularly about the periphery of the ring. It will be understood that although a preferred configuration and means of attachment of the ring and disc have been described, various other configurations and means of attachment may be employed in this preferred embodiment as well. It is required that the attachment between the ring and disc be strong, reliable and leak-proof.

Figure 6:
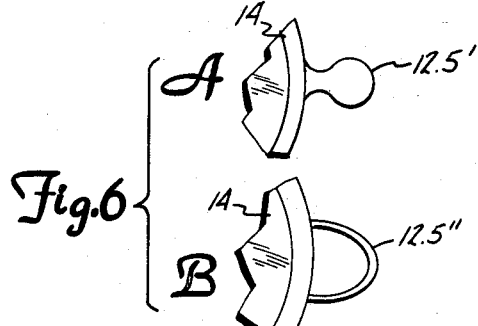
FIG. 6 A and B are broken-away plan views of a modified prosthesis.
Figure 7:
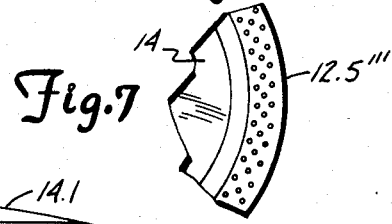
FIG. 7 is a view similar to that of FIG. 6 but showing another modification of the prosthesis.
Figure 5:
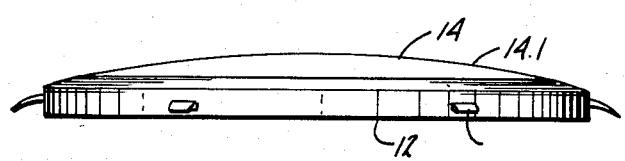
FIG. 5 is a side view of the prosthesis shown also in FIG. 1.

Attachment means, typified as outwardly extending tabs or flanges (12.5), are employed as part of the peripheral portion of the prosthesis to mount it to the rim of an eye from which at least a portion of the cornea has been removed. The flange or flanges (12.5) preferably extend generally radially outwardly from the outer periphery (12.2) of the ring intermediate its height and parallel to the curvature of the eye portion to which they are attached; that is, the flange or flanges are formed at an oblique angle to the axis of the lenticular portion. The flanges are spaced, desirably equiangularly, about the periphery of the ring. In the embodiment shown in FIGS. 1-3, the flanges have a thickness preferably less than one-third of the thickness of the tissue rim to which the ring is to be attached. The flanges may be generally rectangular when viewed from the top, as in FIG. 1, or may be of any other appropriate configuration. For example, the flanges (12.5') may be generally dumbbell in shape (FIG. 6A) or may be formed of small wire loops (FIG. 6B) (12.5") extending outwardly from the outer periphery (12.2) of the ring. The flanges extend outwardly from the ring for a distance sufficient to enable them to be sufficiently deeply embedded within the thickness of the tissue rim as to securely hold the ring in place. Six flanges, equiangularly spaced about the periphery of the ring as shown in FIG. 1 are preferred, although more or fewer flanges may be employed as desired. Also, it will be understood that the use of a plurality of flanges as described above represents a preferred means of attachment of the ring to the tissue rim of an eye; other means of attachment may also be employed. For example, a single, continuous thin flange (12.5''') suitably perforated to receive stitches or to promote tissue ingrowth or both, is shown in FIG. 7.

As explained briefly above, the peripheral, tissue-contacting surface of the prosthesis is of a biologically compatible material such as gold, alloys of high gold content, and other inert materials. Except for the usual symptoms of trauma immediately following implant surgery, the eye should not become inflamed nor should cloudiness or vascular ingrowth of the remaining corneal portion develop, nor should iritis occur, nor should the prosthesis show a tendency to migrate anteriorly or posteriorly of its original implanted position. Desirably, the material forming the tissue-contacting surface of the peripheral portion should support tissue adherance to it during the healing process. The characteristics of certain materials implanted in living tissue have been reported in Venable et al., *A General Consideration of Metals for Buried Appliances in Surgery*, International Abstract of Surgery 76:297-304 (1943); Wolkowicz, et al., *Gold Leaf Seton for Lowering Intraocular Pressure*, Annals of Opthalmology, May, 1971, pp. 527-541, and Bick, *Use of Tantalum for Ocular Drainage*, Archives of Opthalmology 42:373-388 (1949). The most biologically compatible materials generally are opaque.

The surgical methods which are employed for implantation of the prosthesis of the invention are to be very carefully performed, often through the aid of a microscope as is the case with surgical procedures involving donor corneal transplants, nerve reattachments and other types of microsurgery, and the preparations for surgery and the surgical tools employed in the method of the invention are identical or similar to those employed in donor corneal transplant surgery.

Prior to surgery, the diameter of the corneal section to be removed from the eye is determined so that the diseased or damaged portion of the cornea may be removed while leaving a sufficient amount of corneal or corneo-scleral rim material to enable the prosthesis of the invention to be implanted. Also prior to surgery, the prosthesis of the invention is made ready for implantation by suitable sterilization procedures. If desired, the prosthesis may be fabricated at or shortly prior to the time of surgery so that the correct sizing to the individual patient may be accomplished. The diameter of the peripheral portion (12) measured across its outer periphery (12.2), should be the same as or slightly larger than the diameter across the tissue rim remaining after removal of the corneal portion. Should the patient be a child, care is generally taken to make the diameter of the corneal rim as small as practicable so that, as the child grows, the prosthesis of the invention may be replaced with larger prostheses while still maintaining the field of the implant within the bounds of the corneoscleral limbus, subsequent implant procedures ordinarily involving the removal of a small portion of the previously formed corneal rim.

In the implant procedure, the eye is immobilized and the corneal portion to be removed ("B") is excised employing a trephine "T" of the type normally used in corneal transplant procedures. In FIGS. 8-15, "E" represents the eye of a patient, "L" represents the corneoscleral limbus, "C" represents the cornea, "R" represents the rim of the cornea remaining after the removal of the portion ("B"), and "P" (in FIGS. 9 and 11) represents the unaffected pupil of the eye.

Upon completion of the total penetrating keratectomy, the prosthesis of the invention is inserted into the circular space defined by the rim "R", the flanges (12.5) (normally having sharpened ends) being pushed into and becoming imbedded within the thickness of the tissue rim. During the procedure, the prosthesis is supported by a suitable handle or grip such as a small suction cup (not shown) applied to the outer, domed surface of the disc. Care is taken that each of the flanges (12.5) are thus inserted preferably between the posterior one-half and the anterior one-third of the thickness of the tissue rim. Desirably, small sutures ("S" in FIGS. 11 and 12) are taken about each flange and are passed through the cornea to anchor the flanges in place. The generally tight fit between the peripheral portion and the tissue rim assures that no leakage of aqueous humor from the eye will occur. Post-operative procedures are those commonly employed in corneal transplant surgery. It will be noted that the small fingers (12.4) which, in the embodiment of FIG. 4, aid in holding the disc permanently in place within the ring, are quite thin and are feathered toward their outer edges so as to provide minimal irritation to the highly sensitive inner lining of the eyelid.

FIGS. 13-15 show a modification of the procedure described above. Upon removal of a corneal portion "B" as shown in FIG. 9, the surgeon additionally removes a partial thickness annular ring "A" from the outer periphery of the rim "R". In this embodiment, the prosthesis is then gently placed in the rim with the flanges (12.5) resting downwardly against the shoulder "SH" formed by removal of the annular portion "A". The annular portion is then replaced and is sutured to adjacent corneal material by sutures "T" (FIGS. 14 and 15). This procedure may involve less trauma to the rim of tissue and assures proper placement of the flanges (12.5) in the thickness of the corneal rim, as shown in FIG. 14 and as described above.

Various other embodiments will now become evident to those skilled in the art. For example, to improve the liquid-tight seal between the peripheral portion (12) and the tissue rim to which it is affixed, following the procedure depicted in FIGS. 13-15, the peripheral portion of the ring may be provided with a generally downwardly facing, annular shoulder (12.7) shown in FIG. 16 which contacts and rests upon the shoulder "SH" formed in the tissue rim by removal of the annular portion "A".

Although the above discussion has referred for the most part to prosthesis in which the peripheral portion comprised a structural ring of gold or the like, it will now be understood that only the tissue-contacting outer surface of the prosthesis need be of a biologically compatible periphery of the prosthesis may in fact be quite thin and may be applied to the peripheral edge of a lenticule by use of an adhesive, by electroplating or by other methods. The application of gold leaf to various materials is known, for example. FIG. 18 depicts a preferred embodiment of the invention in which the lenticular portion (14) is formed with one or more flanges (14.5) of the type described above, the eye-contacting periphery of the lenticule bearing a thin coating (12.8) of gold or other biologically acceptable material. The coating preferably not only covers the actual tissue-contacting surface, but also extends inwardly of the periphery of the device a short distance, as shown in FIG. 18 and also FIGS. 19 and 20. Either the peripheral portion (12) or the lenticular portion (14), or both, should be sufficiently strong as to provide the prosthesis with resistance to undue bending or tearing. Although the prosthesis may be slightly flexible, it is desired that particularly the lenticular portion (14) be substantially rigid or at least semi-rigid.

As mentioned above, the penetrating keratectomy commonly provides the remaining rim of tissue with walls generally parallel to the visual axis of the eye, and the peripheral exterior tissue-contacting surface of the prosthesis is commonly parallel to the axis of the lenticular portion (excluding the flanges (12.5), (14.5)) to provide surface-to-surface contact with the tissue walls. If desired, however, the tissue-contacting surface of the prosthesis may be provided with other configurations to best suit the particular tissue rim. If the rim of tissue is particularly thick, for example, one may desire to use a prosthesis with a generally convex or outwardly rounded periphery, as shown in FIG. 19. Similarly, one may wish to employ a prosthesis having a concave or grooved periphery as shown in FIG. 20 if the tissue rim is particularly thin.

In FIG. 17, which diagrammatically depicts the anterior portion of the human eye, the cornea is represented as "C", the sclera (and associated structures such as the conjunctiva, Tenons (Capsule, epischlera and choroid, not separately shown) by "SCH", the iris by "I", the ciliary body by "CB" and Schwabe's Line by "SL". Three proposed locations of the prosthesis are shown. In the first, only the central corneal "button" is removed and replaced by the prosthesis; dashed line "CC" locates the boundary of the keratectomy. In the second, the boundary of the keratectomy is in the peripheral corneal area and is designated "PC". In the third, boundary of the keratectomy is adjacent the limbo-scleral ring "LSR" in the corneo-scleral portion of the eye and is designated "CS". To avoid damage to the aqueous humor drainage mechanism, it is recommended that the internal boundary of the keratectomy not be carried posteriorly of Schwabe's Line "SL", although the flange (12.5) may project as desired into the sclera.

Each position shown in FIG. 17 has certain advantages and disadvantages. For example, replacement of the central corneal button may limit peripheral vision slightly and the risk of failure of the operation is increased; yet, assuming that the corneal rim is not damaged, this location may permit subsequent implant or transplant procedures to be performed. The corneoschleral position appears least likely to fail and may be cosmetically superior, but such position severely limits repeat implants or transplants.

The prosthesis and method of the invention may be employed not only as a temporary, sealing, visionproviding measure while the availability of a natural donor cornea is awaited, but also as a permanent implant, particularly with older patients or for patients unable, because of immune reactions, to tolerate donor corneas.

As mentioned above, the lenticular portion (14) may function as a lens for the purpose of correcting vision, and may be particularly valuable as a replacement for a natural lens that has been removed through cataract surgery.

While a preferred embodiment of the present invention has been described, it should be understood that various changes, adaptations and modifications may be made therein without departing from the spirit of the invention and the scope of the appended claims.

I claim:

1. A corneal implant prosthesis having a transparent lenticule having a ring-shaped periphery provided with flange means extending generally radially outwardly therefrom for attachment to the sclera of the eye wall beyond the limbo-scleral ring, the peripheral ring, including flange means, bearing a thin coating of a biologically acceptable material providing a tissue-contacting surface.

2. The prosthesis of claim 1 wherein the flange means is formed with sharp peripheral edges and extends at an oblique angle to the plane ring.

3. The prosthesis of claim 1 wherein the flange means include perforations of sufficient size as to permit tissue ingrowth therethrough.

4. The prosthesis of claim 1 wherein the flange means comprises a plurality of flanges extending radially outwardly of the periphery of the ring and adapted to be imbedded within the thickness of the frontal eye wall, the flanges being spaced about the periphery of the ring.

5. The prosthesis of claim 1 wherein the ring has walls of uniform height measured parallel to the ring axis and wherein said flange means protrudes outwardly of the ring intermediate said height.

6. Surgical corneal replacement procedure comprising the steps of:
 (a) performing a keratectomy, leaving a generally circular rim of tissue;
 (b) surgically removing from the tissue rim an interior, partial thickness annular section;
 (c) providing a corneal prosthesis comprising a transparent disc-like lenticule of biologically acceptable material, an annular ring extending about and secured to the periphery of the disc with a liquid-tight seal, the ring having flange means at its periphery for attaching the same to the remaining tissue rim; and
 (d) placing the prosthesis in the tissue rim with the flange means of the annular ring laying against the outwardly-facing shoulder formed by removal of the annular tissue section, and replacing the annular tissue section to capture the flange means between the tissue section and the shoulder.

7. Surgical procedure comprising the steps of:
 (a) surgically removing at least a portion of the cornea of the eye providing a tissue rim adjacent the limbo-scleral ring;
 (b) providing a prosthesis comprising a transparent, disc-like lenticule of biologically acceptable material and having flange means at its periphery;
 (c) placing the prosthesis within the tissue rim with the flange means extending into the sclera beyond the limbo-scheral ring, and attaching the flange means to the scheral tissue.

8. The method of claim 7 wherein the flange means of said prosthesis comprises a plurality of flanges extending generally radially outwardly of the periphery of the ring, the method including the step of imbedding said plurality of flanges within the thickness of the frontal eye wall in the sclera beyond the limbo-scleral ring.

9. The method of claim 7 wherein the flange means includes perforations of sufficient size as to permit scleral tissue ingrowth therethrough, the method including the step of positioning said flange within the thickness of the scleral wall so as to permit scheral ingrowth through said perforations.

* * * * *